United States Patent
Putha et al.

(10) Patent No.: US 10,733,727 B2
(45) Date of Patent: Aug. 4, 2020

(54) APPLICATION OF DEEP LEARNING FOR MEDICAL IMAGING EVALUATION

(71) Applicant: Qure.AI Technologies Private Limited, Mumbai (IN)

(72) Inventors: Preetham Putha, Mumbai (IN); Manoj Tadepalli, Mumbai (IN); Bhargava Reddy, Mumbai (IN); Tarun Nimmada, Mumbai (IN); Pooja Rao, Mumbai (IN); Prashant Warier, Mumbai (IN)

(73) Assignee: Qure.AI Technologies Private Limited, Mumbai (IN)

( * ) Notice: Subject to any disclaimer, the term of this patent is extended or adjusted under 35 U.S.C. 154(b) by 0 days.

(21) Appl. No.: 16/268,694

(22) Filed: Feb. 6, 2019

(65) Prior Publication Data

US 2020/0151871 A1 May 14, 2020

Related U.S. Application Data

(63) Continuation of application No. PCT/IB2019/050317, filed on Jan. 15, 2019.

(30) Foreign Application Priority Data

Nov. 14, 2018 (IN) .............................. 201821042893

(51) Int. Cl.
*G06K 9/00* (2006.01)
*G06T 7/00* (2017.01)
(Continued)

(52) U.S. Cl.
CPC ............ *G06T 7/0012* (2013.01); *A61B 6/503* (2013.01); *A61B 6/5217* (2013.01); *G06F 40/30* (2020.01);
(Continued)

(58) Field of Classification Search
None
See application file for complete search history.

(56) References Cited

U.S. PATENT DOCUMENTS 7,676,076 B2    3/2010   Spahn
8,483,831 B1 *   7/2013   Hlavka ................ A61B 5/0823
                                                                                              607/42

(Continued)

FOREIGN PATENT DOCUMENTS

KR           101887194         8/2018

OTHER PUBLICATIONS

Shin, Hoo-Chang, et al. "Learning to read chest x-rays: Recurrent neural cascade model for automated image annotation." Proceedings of the IEEE conference on computer vision and pattern recognition. 2016. (Year: 2016).*

(Continued)

*Primary Examiner* — Sean M Conner
(74) *Attorney, Agent, or Firm* — Wiley Rein LLP

(57) ABSTRACT

This disclosure generally pertains to methods and systems for processing electronic data obtained from imaging or other diagnostic and evaluative medical procedures. Certain embodiments relate to methods for the development of deep learning algorithms that perform machine recognition of specific features and conditions in imaging and other medical data. Another embodiment provides systems configured to detect and localize medical abnormalities on medical imaging scans by a deep learning algorithm.

11 Claims, 5 Drawing Sheets

(51) Int. Cl.
*G06T 7/73* (2017.01)
*A61B 6/00* (2006.01)
*G06N 3/08* (2006.01)
*G06F 40/30* (2020.01)

(52) U.S. Cl.
CPC .............. *G06N 3/08* (2013.01); *G06T 7/73* (2017.01); *G06T 2207/10116* (2013.01); *G06T 2207/20081* (2013.01)

(56) References Cited

U.S. PATENT DOCUMENTS

| | | | |
|---|---|---|---|
| 10,111,632 B2 | 10/2018 | Anavi | |
| 2001/0021264 A1* | 9/2001 | Armato, III | G06K 9/38 382/132 |
| 2002/0094119 A1* | 7/2002 | Sahadevan | G06T 7/0012 382/132 |
| 2003/0186904 A1* | 10/2003 | Ruben | C07K 14/50 514/44 R |
| 2012/0008838 A1* | 1/2012 | Guyon | G06T 7/0012 382/128 |
| 2013/0251207 A1* | 9/2013 | Mukhopadhyay | G06T 7/0012 382/103 |
| 2016/0350919 A1 | 12/2016 | Steigauf | |
| 2016/0364857 A1 | 12/2016 | Reicher | |
| 2018/0068083 A1 | 3/2018 | Cohen | |
| 2019/0050981 A1* | 2/2019 | Song | G06T 7/0012 |
| 2019/0197395 A1* | 6/2019 | Kibune | G06N 3/08 |
| 2019/0340763 A1* | 11/2019 | Laserson | G06N 3/00 |

OTHER PUBLICATIONS

Walczak, Steven, and Narciso Cerpa. "Heuristic principles for the design of artificial neural networks." Information and software technology 41.2 (1999): 107-117. (Year: 1999).*
Rubin, Jonathan, et al. "Large scale automated reading of frontal and lateral chest x-rays using dual convolutional neural networks." arXiv preprint arXiv:1804.07839 (2018). (Year: 2018).*
Krizhevsky, Alex, Ilya Sutskever, and Geoffrey E. Hinton. "Innagenet classification with deep convolutional neural networks." Advances in neural information processing systems. 2012. (Year: 2012).*
Caruana, Rich, et al. "Ensemble selection from libraries of models." Proceedings of the twenty-first international conference on Machine learning. ACM, 2004. (Year: 2004).*
PlosOne Research Article Oct. 4, 2018; 13(10). Deep learning in chest radiography: Detection of findings and presence of change. Ramandeep Singh.
Can Artificial Intelligence Reliably Report Chest X-Rays?: Radiologist Validation of an Algorithm trained on 2.3 Million X-Rays. Preetham Putha et al. Jul. 19, 2018.
ChestX-ray8: Hospital-scale Chest X-ray Database and Benchmarks on Weakly-Supervised Classification and Localization of Common Thorax Diseases. Xiaosong Wang et al. Dec. 14, 2017.
International Search Report issued in PCT/IB19/50317 dated Aug. 5, 2019.
Written opinion of the international searching authority issued in PCT/IB19/50317 dated Aug. 5, 2019.
Extended European Search Report issued in EP19156986.2 dated Aug. 2, 2019.

* cited by examiner

APPLICATION OF DEEP LEARNING FOR MEDICAL IMAGING EVALUATION

RELATED APPLICATIONS

This application claims priority benefit of International Application No. PCT/IB2019/050317, filed Jan. 15, 2019, which claims priority benefit of Indian Patent Application No. 201821042893, filed Nov. 14, 2018, which are incorporated entirely by reference herein for all purposes.

TECHNICAL FIELD

This disclosure generally pertains to methods and systems for processing electronic data obtained from imaging or other diagnostic and evaluative medical procedures. Some embodiments relate to methods for the development of deep learning algorithms that perform machine recognition of specific features and conditions in imaging and other medical data.

BACKGROUND ART

Medical imaging techniques, such as computed topography (CT) and X-ray imaging, are widely used in diagnosis, clinical studies and treatment planning. There is an emerging need for automated approaches to improve the efficiency, accuracy and cost effectiveness of the medical imaging evaluation.

Chest X-rays are among the most common radiology diagnostic tests, with millions of scans performed globally every year. While the test is frequently performed, reading chest X-rays is among the more complex radiology tasks, and is known to be highly subjective, with inter-reader agreement varying from a kappa value of 0.2 to 0.77, depending on the level of experience of the reader, the abnormality being detected and the clinical setting.

Due to their affordability, chest X-rays are used all over the world, including in areas with few or no radiologists. In many parts of the world, the availability of digital chest X-ray machines is growing more rapidly than the availability of clinicians who are trained highly enough to perform this complex task. If automated detection can be applied in low-resource settings as a disease screening tool, the benefits to population health outcomes globally could be significant. One example of such use of chest X-rays is in tuberculosis screening, where chest X-rays, in the hands of expert readers are more sensitive than clinical symptoms for the early detection of tuberculosis.

Over the last few years, there has been increasing interest in the use of deep learning algorithms to assist with abnormality detection on medical images. This is a natural consequence of the rapidly growing ability of machines to interpret natural images and detect objects in them. On chest X-rays in particular, there have been a series of studies describing the use of deep learning algorithms to detect various abnormalities (Shin, et al., *Proceedings of the IEEE Conference on Computer Vision and Pattern Recognition*, pages 2497-2506, 2016; Rajpurkar, et al, arXiv preprint arXiv:1711.05225, 2017; Li, et al., arXiv preprint arXiv: 1711.06373, 2017). Most of these have been limited by the lack of availability of large high-quality datasets, with the largest published work describing an algorithm that has been trained with 112,120 X-rays, a relatively small number considering that the majority of chest X-rays are normal, and abnormal X-rays are less common, with specific abnormalities being rarer still.

SUMMARY OF THE INVENTION

The present disclosure describes the development and clinical validation of fully automated deep learning systems that are trained to detect and localize abnormalities from medical imaging scans.

Certain embodiment provides the training and clinical validation of a deep learning system to detect and localize chest X-ray abnormalities. The system has been trained on 1.2 million X-rays and tested it against the majority vote of a panel of 3 radiologists on an independent dataset containing 2000 studies. Abnormalities on chest X-rays range from very small lesions to diffuse abnormalities that cover large parts of the lung field. The optimal deep learning algorithm architecture differs based on the abnormality being detected; hence a system that uses an individual algorithm with maximized AUC for each abnormality is provided.

In particular, an embodiment provides a method for developing a deep learning system to detect and localize medical abnormalities on chest X-ray scans comprising:

Selecting medical imaging scans and extracting medical abnormalities using natural language processing (NLP) algorithms;

Pre-processing the selected medical imaging scans by resizing and tag-specific data augmentations;

Training a deep learning algorithm comprising a convolutional neural network architecture with the selected medical imaging scans, wherein the architecture is modified by pre-training on a task of separating chest X-ray scans from X-ray scans of other body parts;

Predicting the presence/absence of a particular type of medical abnormalities by combining the predictions of multiple models, wherein the models are selected using various heuristics;

Generating a score that corresponds to a level of recognition of the medical abnormalities and outputting a bounding box representing the precise location and extent of the medical abnormalities; and Validating the accuracy of the deep learning algorithm for detecting the medical abnormalities by comparing with the radiologist reports.

According to an embodiment, the said medical imaging scans include but not limited to CT, X-ray, magnetic resonance imaging (MRI), and ultrasound procedures. For chest X-ray scans, the said medical abnormalities include but not limited to blunted CP angle, calcification, cardiomegaly, cavity, consolidation, fibrosis, hilar enlargement, opacity and pleural effusion.

Another embodiment provides a system configured to detect and localize medical abnormalities on chest X-ray scans by a deep learning algorithm, wherein the deep learning algorithm is developed by the steps of:

Selecting medical imaging scans and extracting medical abnormalities using natural language processing (NLP) algorithms;

Pre-processing the selected medical imaging scans by resizing and tag-specific data augmentations.

Training the deep learning algorithm comprising convolutional neural network architecture with the selected medical imaging scans, wherein the architecture is modified by pre-training on a task of separating chest X-ray scans from X-ray scans of other body parts;

Predicting the presence/absence of a particular type of medical abnormalities by combining the predictions of multiple models, wherein the models are selected using various heuristics;

Generating a score that corresponds to a level of recognition of the medical abnormalities and outputting a bounding box representing the precise location and extent of the medical abnormalities; and Validating the accuracy of the deep learning algorithm for detecting the medical abnormalities by comparing with the radiologist reports.

Further, a system configured to detect and localize medical abnormalities on chest X-ray scans by a deep learning algorithm, wherein the algorithm achieves AUC of 0.93±0.01 for detection of abnormal scans, and AUCs of 0.94±0.02, 0.88±0.03, 0.97±0.02, 0.93±0.07, 0.93±0.04, 0.88±0.05, 0.89±0.05, 0.93±0.02, 0.98±0.02 for the detection of blunted costophrenic angle, calcification, cardiomegaly, cavity, consolidation, fibrosis, hilar enlargement, opacity and pleural effusion, respectively.

Advantageous Effects of the Invention

Previous published work on deep learning for chest X-ray abnormality detection has not made a distinction between the diagnosis of "diseases" and the detection of "abnormal findings". The present invention is to focus on the detection of abnormal findings, or abnormalities on the X-ray that can be detected visually by an expert without any prior knowledge of clinical history. This allows the system to be applied across geographical settings with different disease prevalence patterns and across different disease manifestations.

DETAILED DESCRIPTION

Figure 1:
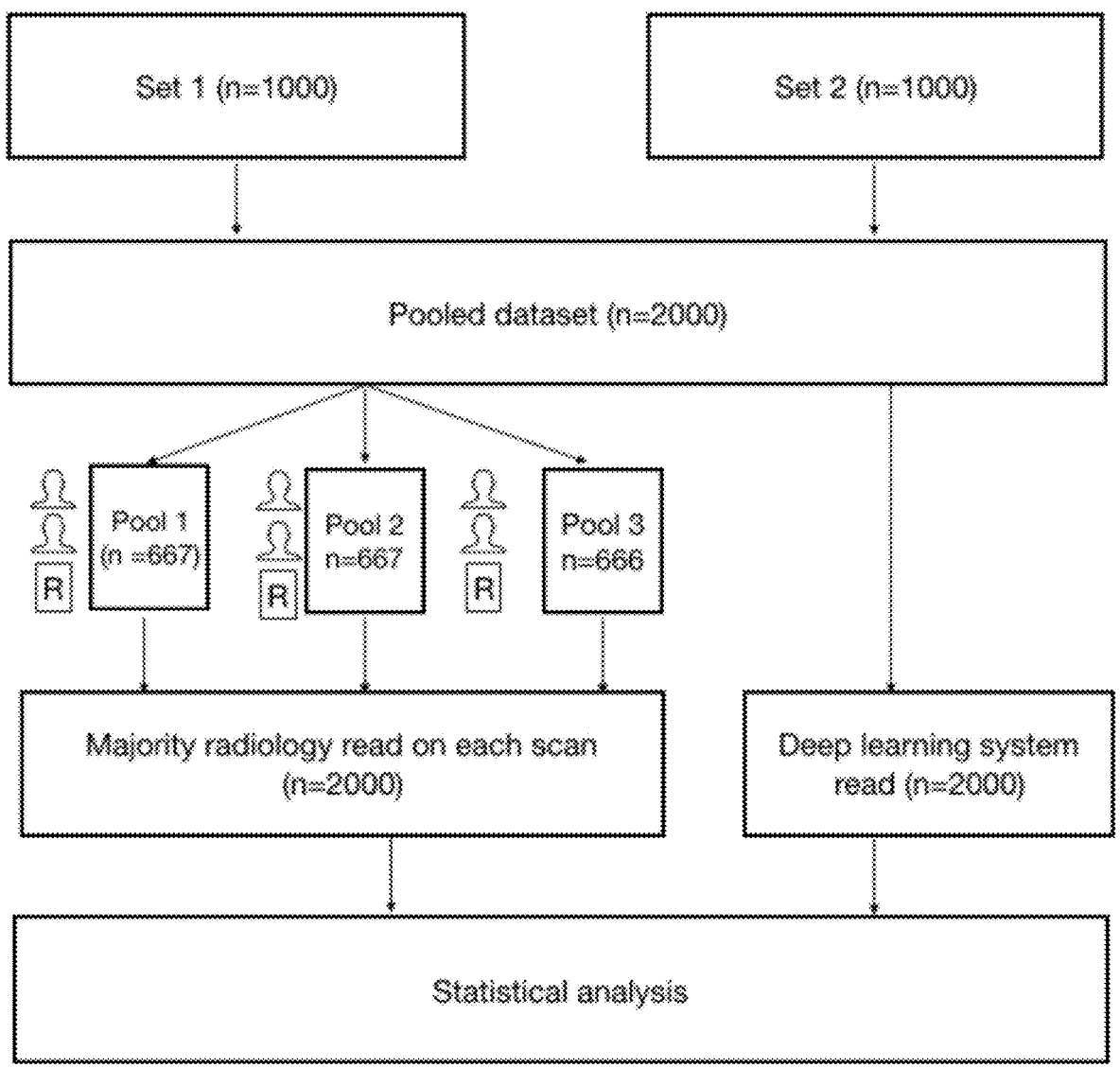
FIG. 1 Study design for radiologist validation of a deep learning system to detect chest X-ray abnormalities.

It should be understood that this invention is not limited to the particular methodology, protocols, and systems, etc., described herein and as such may vary. The terminology used herein is for the purpose of describing particular embodiments only, and is not intended to limit the scope of the present invention, which is defined solely by the claims.

As used in the specification and appended claims, unless specified to the contrary, the following terms have the meaning indicated below.

"Architecture" refers to a set of rules and methods that describe the functionality, organization, and implementation of computer systems.

"Convolutional neural network (CNN)" refers to a class of deep, feed-forward artificial neural networks, most commonly applied to analyzing visual imagery. CNNs use a variation of multilayer perceptrons designed to require minimal preprocessing. A CNN consists of an input and an output layer, as well as multiple hidden layers. The hidden layers of a CNN typically consist of convolutional layers, pooling layers, fully connected layers and normalization layers. Convolutional layers apply a convolution operation to the input, passing the result to the next layer. Local or global pooling layers combine the outputs of neuron clusters at one layer into a single neuron in the next layer. Fully connected layers connect every neuron in one layer to every neuron in another layer. CNNs use relatively little pre-processing compared to other image classification algorithms. This means that the network learns the filters that in traditional algorithms were hand-engineered. This independence from prior knowledge and human effort in feature design is a major advantage.

"Heuristics" refers to a technique designed for solving a problem more quickly when classic methods are too slow, or for finding an approximate solution when classic methods fail to find any exact solution. This is achieved by trading optimality, completeness, accuracy, or precision for speed. In a way, it can be considered a shortcut. A heuristic function, also called simply a heuristic, is a function that ranks alternatives in search algorithms at each branching step based on available information to decide which branch to follow. The objective of a heuristic is to produce a solution in a reasonable time frame that is good enough for solving the problem at hand. This solution may not be the best of all the solutions to this problem, or it may simply approximate the exact solution.

"Natural language processing (NLP)" refers to a way for computers to analyze, understand, and derive meaning from human language in a smart and useful way. By utilizing NLP, developers can organize and structure knowledge to perform tasks such as automatic summarization, translation named entity recognition, relationship extraction, sentiment analysis, speech recognition, and topic segmentation.

The present disclosure illustrates various techniques and configurations that enable the integration and use of machine learning analysis in a data-driven image evaluation workflow. For example, machine learning analysis (such as trained models of image detection of certain medical conditions) may be performed upon medical imaging procedure data produced as part of a medical imaging study. The medical imaging procedure data may include image data captured by an imaging modality, and order data (such as data indicating a request for a radiological image read), each produced to facilitate a medical imaging evaluation (such as a radiology read to be performed by a radiologist or a diagnostic evaluation by another qualified medical professional).

For example, the machine learning analysis may receive and process images from medical imaging procedure data, to identify trained structures, conditions, and conditions within images of a particular study. The machine learning analysis may result in the automated detection, indication, or confirmation of certain medical conditions within the images, such as the detection of urgent or life-critical medical conditions, clinically serious abnormalities, and other key findings. Based on the result of the machine learning analysis, the medical evaluation for the images and the associated imaging procedure may be prioritized, or otherwise changed or modified. Further, the detection of the medical conditions may be used to assist the assignment of the medical imaging data to particular evaluators, the evaluation process for the medical imaging data, or implement other actions prior to, or concurrent with, the medical imaging evaluation (or the generation of a data item such as a report from such medical imaging evaluation).

As further discussed herein, the machine learning analysis may be provided on behalf of any number of machine learning algorithms and trained models, including but not limited to deep learning models (also known as deep machine learning, or hierarchical models) that have been trained to perform image recognition tasks, particularly for certain types of medical conditions upon medical images of human anatomy and anatomical representations. As used herein, the term "machine learning" is used to refer to the various classes of artificial intelligence algorithms and algorithm-driven approaches that are capable of performing machine-driven (e.g., computer-aided) identification of trained structures, with the term "deep learning" referring to a multiple-level operation of such machine learning algorithms using multiple levels of representation and abstraction. However, it will be apparent that the role of the machine learning algorithms that are applied, used, and configured in the presently described medical imaging evaluation may be supplemented or substituted by any number of other algorithm-based approaches, including variations of artificial neural networks, learning-capable algorithms, trainable object classifications, and other artificial intelligence processing techniques.

In some of the following examples, reference is made to radiology medical imaging procedures (e.g., computed tomography (CT), magnetic resonance imaging (MRI), Ultrasound, and X-ray procedures, etc.) and diagnostic evaluation of the images produced from such imaging procedures that would be performed with an image evaluation (e.g., radiology read) by a licensed and credentialed radiologist. It will be understood that the applicability of the presently described techniques and systems will extend to a wide variety of imaging data (and other data representations) produced by various medical procedures and specialties, including those not involving traditional radiology imaging modalities. Such specialties include, but are not limited, to pathology, medical photography, medical data measurements such as electroencephalography (EEG) and electrocardiography (EKG) procedures, cardiology data, neuroscience data, preclinical imaging, and other data collection procedures occurring in connection with telemedicine, telepathology, remote diagnostics, and other applications of medical procedures and medical science. Accordingly, the performance of the data recognition and workflow modification techniques described herein may apply to a variety of medical image data types, settings, and use cases, including captured static images and multi-image (e.g. video) representations.

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments.

EXAMPLES

Example 1. Radiologist Validation of a Deep Learning System to Detect Chest X-Ray Abnormalities 1.1 Methods
1.1.1 Algorithm Development 1,200,000 X-rays and their corresponding radiology reports were used to train convolutional neural networks (CNNs) to identify the abnormalities. Natural language processing algorithms were developed to parse unstructured radiology reports and extract information about the presence of abnormalities in the chest X-ray. These extracted findings were used as labels when training CNNs. Individual networks were trained to identify normal X-rays, and the chest X-ray findings 'blunted CP angle', 'calcification', 'cardiomegaly', 'cavity', 'consolidation', 'fibrosis', 'hilar enlargement', 'opacity' and 'pleural effusion'. Table 1 lists definitions that were used when extracting radiological findings from the reports. These findings were referred as tags. Tag extraction accuracy was measured versus a set of reports where abnormalities were manually extracted. Tag extraction accuracy is reported in Table 2a.

TABLE 1

Abnormality definitions

| Finding | Definition for tag extraction from radiology reports | Definition for radiologist review |
|---|---|---|
| Normal | 'No abnormality detected' or 'Normal' | Normal X-ray |
| Blunted CP angle | Blunted CP angle | CP Angle blunted or obscured. Could be due to pleural effusion or pleural thickening |
| Calcification | Calcification | All calcifications on X-ray including but not limited to aortic arch calcification, rib calcifications, calcified pulmonary densities and microcalcifications |
| Cardiomegaly | Cardiomegaly | Cardiothoracic ratio >0.5 |
| Cavity | Pulmonary cavity | Pulmonary cavity |
| Consolidation | Consolidation, pneumonia or air-bronchogram | Pulmonary consolidation |
| Fibrosis | Fibrosis | Any evidence of lung fibrosis, including interstitial fibrosis, fibrocavitary lesion |
| Hilar prominence | Hilar enlargement, prominent hilum or hilar lymphadenopathy | Enlarged or prominent hilum or including hilar lymphadenopathy |
| Opacity | Any lung field opacity or opacities, shadow or density including but not limited to infiltrate, consolidation, mass, nodule, pulmonary calcification, and fibrosis | Any lung field opacity or multiple opacities including but not limited to infiltrate, consolidation, mass, nodule, pulmonary calcification, and fibrosis. Pleural abnormalities not included under this tag |
| Pleural Effusion | Pleural Effusion | Pleural Effusion |

TABLE 2

Tagextraction accuracy.

| Finding | #Positives | Sensitivity (95% CI) | Specificity (95% CI) |
|---|---|---|---|
| Normal (No abnormality detected) | 105 | 0.9429 (0.8798-0.9787) | 1.0000 (0.9959-1.0000) |
| Blunted CP angle | 146 | 0.9795 (0.9411-0.9957) | 0.9824 (0.9712-0.9901) |
| Calcification | 116 | 1.0000 (0.9687-1.0000) | 0.9660 (0.9519-0.9770) |
| Cardiomegaly | 125 | 0.9920 (0.9562-0.9998) | 0.9760 (0.9635-0.9851) |
| Cavity | 30 | 1.0000 (0.8843-1.0000) | 0.9856 (0.9759-0.9921) |
| Consolidation | 161 | 0.9876 (0.9558-0.9985) | 0.9761 (0.9634-0.9854) |
| Fibrosis | 124 | 0.9839 (0.9430-0.9980) | 0.9931 (0.9851-0.9975) |
| Hilar Enlargement | 289 | 0.9689 (0.9417-0.9857) | 0.9732 (0.9585-0.9838) |
| Opacity | 612 | 0.9608 (0.9422-0.9747) | 0.9251 (0.8942-0.9492) |
| Pleural Effusion | 246 | 0.9309 (0.8917-0.9592) | 0.9602 (0.9436-0.9730) |
| Total (all findings) | 1954 | 0.9672 (0.9584-0.9747) | 0.9771 (0.9736-0.9803) |

(a) Tag Extraction Accuracies

| | Radiologist 1 & 2 | | All reads |
|---|---|---|---|
| Finding | Agreement % | Cohen's κ | Fleiss' κ |
| Normal (No abnormality detected | 85.00 | 0.6049 | 0.5618 |
| Blunted CP angle | 83.58 | 0.2968 | 0.3054 |
| Calcification | 83.00 | 0.5803 | 0.5821 |
| Cardiomegaly | 91.60 | 0.5333 | 0.5284 |
| Cavity | 97.50 | 0.3824 | 0.4047 |
| Consolidation | 88.28 | 0.3529 | 0.3397 |
| Fibrosis | 89.40 | 0.3781 | 0.3495 |
| Hilar Enlargement | 89.38 | 0.2630 | 0.2101 |
| Opacity | 70.70 | 0.2306 | 0.1733 |
| Pleural Effusion | 90.69 | 0.5341 | 0.5305 |

(b) Interradiologist Concordance. Fleiss' κ is calculated between the two radiologist reads and the ground truths extracted from original reports with NLP.

1.1.1.1 Pre-Processing and Data Augmentation

All X-rays were resized to a standard size and a set of standard normalizations were applied to reduce source dependent variation. The resizing operation involves downsampling the original images. Though downsampling implies loss of potentially valuable information, It helps models to train better by overcoming the curse of dimensionality and is warranted by the current state of AI. Additionally, the size of the image impacts the speed of inference significantly.

Given the fact that X-Rays are not as standardized as other medical imaging modalities like CTs and MRIs, A large number of tag specific data augmentations aimed at making the models robust to variability in manufacturer/model used to acquire, exposure, noise are used while training.

1.1.1.2 Architectures and Training

The basic blocks in the systems that detect individual abnormalities are modified versions of either densenets (Huang, et al., *Proceedings of the IEEE conference on computer vision and pattern recognition*, volume 1, page 3, 2017) or resnets (He, et al., *Proceedings of the IEEE conference on computer vision and pattern recognition*, pages 770-778, 2016). All the classification models that build up the individual abnormality detection systems are pre-trained on the task of separating chest x-rays from x-rays of other body parts rather than the popular ImageNet pre-training. This step is aimed at making use of the super-set consisting of all the x-rays. Improved model convergence and incremental gains in generalization performance were observed when compared to ImageNet pre-training.

1.1.1.3 Use of Model Ensembles

Ensembling is a simple way of improving generalization performance by combining the predictions produced by a set of models. Multiple models are created to detect a particular abnormality using different initial conditions, architectures and sampling (the distribution of abnormalities that are used while training). A subset of these models are selected using various heuristics and a majority ensembling scheme is used to combine the predictions of these selected models to make a decision about the presence/absence of a particular abnormality.

1.2 Study Design

1.2.1 Sample Size and X-Ray Selection

A combination of out-patient and in-hospital X-rays from 2 Columbia Asia Hospital centers in South India were used for the study. All data were de-identified before use in this study. Radiologist validation was performed in 2 phases, using a separate set of 1000 X-rays for each phase. Sample size calculations are explained in Section 1.4.1 All Chest X-rays from both centres were filtered as follows.

1. All PA and AP view Chest X-rays where a radiologist report was available were selected.
2. Of this set, X-rays from pediatric patients (age≤14 years), X-Rays taken with the supine position (bedside/portable X-rays) were excluded.

A set of 1000 X-rays (Set 1) was selected randomly from this pool, with no enrichment of X-rays containing the abnormalities of interest. A second set of 1000 X-rays (Set 2) were sampled from the same pool (excluding the previously selected 1000 X-rays) such that they included at least 80 examples of each abnormality where available, with the remaining X-rays being randomly selected. A natural language processing tool that parsed the X-ray radiology reports was used to implement the exclusions listed above, and to automate the sampling for phase 2. The study design is illustrated in FIG. 1.

1.2.2 Inclusion and Exclusion Criteria

PA and AP view chest X-rays from ambulatory adult patients taken in the standing position were included in the study. X-rays from patients under 14 years old, X-rays taken in the supine position, from bedside or portable X-ray machines were excluded. As a result, the datasets did not contain any X-rays with visible intravenous lines, tubes or catheters or ECG leads or X-rays from patients with implanted medical devices such as pacemakers.

1.2.3 Abnormality Definitions

To ensure that reviewing radiologists and the algorithm were operating from the same frame of reference for defining abnormalities, the following working definitions were used for 'normal' and for each abnormality. These definitions were used for extraction of tags from reports during the algorithm development phase and by the radiologists during the validation phase.

1.3 Radiologist Validation and Gold Standard Creation 1.3.1 Abnormality Extraction from Reports A custom dictionary-based approach, combined with natural language processing algorithms was used to extract the relevant findings from the original radiologist reports corresponding to the X-rays. The accuracy of natural language processing algorithms was quantified for extracting chest X-ray abnormalities from unstructured radiology reports on an independent dataset consisting of 2000 scans, versus the opinion of a single expert reader for each scan. The experts were provided with the tag definitions in Table 1, the original reports, along with the chest X-rays, and were blinded to the algorithm output.

1.3.2 Validation of Deep Learning Algorithm Accuracy for Abnormality Detection from Images The X-rays were randomly divided among 6 of board-certified radiologists (3 pairs), with between 3 and 15 years of radiology expertise such that each X-ray was independently read by 2 radiologists, neither of whom had originally reported that X-ray. A third read was available in the form of the original radiology report accompanying the X-ray. A custom validation portal was used for the radiologist validation. The DICOM file was available in full original resolution for radiologists to use while deciding on the presence of abnormalities. Radiologists were enabled to mark 'present' or 'absent' for each abnormality, as well as to use a pen tool to mark out the area affected. An additional text field was available for feedback.

The gold standard for this study was the majority opinion on the presence or absence of each abnormality between 3 radiologist reads (2 radiologists using the validation portal for retrospective evaluation and 1 original radiology report). Algorithm accuracy on detecting abnormal X-rays and on each individual abnormality is reported versus this gold standard. Algorithm output was generated on both datasets and placed in a locked database, until completion of the radiologist validation. Radiologists were blinded to the original X-ray report and the algorithm output when reviewing the X-rays for the validation study.

1.4 Statistical Analysis 1.4.1 Sample Size Calculation

Calculating sensitivity and specificity precisely with a 95% confidence interval would require a sample size of approximately 20,000 in an un-enriched dataset randomly sampled from the population. The enrichment strategy detailed in Section 1.2.1 was used. The sample required to estimate the 80% sensitivity with 90% accuracy and 95% confidence interval is 951. Therefore 2000 X-rays would be sufficient to evaluate the classification of X-rays as normal and abnormal. Sensitivity is considered for this sample size calculation as a false negative is considered more serious than false positive in preliminary diagnostic investigations.

The abnormalities have a prevalence of less than 5% in the typical outpatient setting. A sample size of 951 X-rays would give 3% precision for estimating 80% specificity at 95% confidence interval. Given a prevalence of less than 10% for each of the specific conditions listed above, at least 77 true cases per condition would give a sensitivity of 80% with 10% precision and 95% confidence interval. Therefore, a minimum of 80 true cases per condition was used for Set 2.

1.4.2 Algorithm Performance Measurements Versus Radiologists

When calculating AUC for a particular abnormality, Set 1 in its entirety, and all the X-rays positive for that abnormality from Set 2 were used.

1. Use a sufficiently large number of 'abnormality-positive' cases for sensitivity calculation.
2. Keep the ratio of Normals:Abnormals close to the natural distribution. This enables a fairer estimation of specificity when compared to using both the sets combined.

In effect, this is equivalent to performing independent studies evaluating the accuracy of detection of each abnormality separately. However, the entire dataset (n=2000) was used when calculating AUC for detection of abnormal X-rays.

AUC confidence intervals were calculated using the 'distribution-based' method described by Hanley and McNeil (*Radiology*, 143(1):29-36, 1982). The concordance between paired readers on each finding was measured using percentage of agreement and the Cohen's kappaκ statistic (*Fam Med*, 37(5):360-363, 2005). In addition, concordance between all the three readers (2 radiologists and the original report) on each finding was measured using Fleiss' kappaκ statistic (*Psychological bulletin*, 76(5):378, 1971). Since readers were grouped into 3 pairs, each reported measures of inter-reader agreement is the average of 3 estimates.

1.3 Results

Basic demographics and the number of scans containing each abnormality are summarized in Table 3. 658 out of 2000 X-rays were abnormal, with the most frequent abnormalities being 'opacity', 'cardiomegaly' and 'calcification'. There were not enough scans containing a cavity to confidently calculate the accuracy of the deep learning system at identifying this abnormality.

TABLE 3

Demographics of the study population.

| Characteristic | Set1 (n = 1000) | Set2 (n = 1000) | Combined (n = 2000) |
|---|---|---|---|
| PATIENT DEMOGRAPHIC | | | |
| Age | | | |
| No. of scans for which age was known | 803 | 1000 | 1803 |
| Mean | 48.04 | 50.61 | 49.32 |
| Standard deviation | 18.69 | 17.93 | 18.36 |
| Range | 16-95 | 16-100 | 16-100 |
| No. of females/No. of scans for which sex was known (percentage) | 324/803 (40.3%) | 265/1000 (26.5%) | 589/1803 (32.6%) |
| PREVALENCE | | | |
| No. of scans (percentage) with | | | |
| No abnormality detected (Normal) | 440 | 218 | 658 |
| Blunted CP angle | 35 | 121 | 156 |
| Calcification | 57 | 244 | 301 |
| Cardiomegaly | 61 | 116 | 177 |
| Cavity | 1 | 15 | 16 |
| Consolidation | 13 | 92 | 105 |
| Fibrosis | 13 | 97 | 110 |
| Hilar enlargement | 15 | 49 | 64 |
| Opacity | 104 | 341 | 445 |
| Pleural Effusion | 36 | 122 | 158 |

Achieving a high accuracy on report parsing was instrumental to being able to use a large number of X-rays to train the deep learning algorithms. Abnormality extraction accuracy from radiology reports versus manual extraction by a single reader is summarized in Table 2a. The algorithm was able to detect normal X-ray reports with a sensitivity of 0.94 and a specificity of 1 versus the expert reader. For detection of individual abnormalities from reports, sensitivity varied from 0.93 for pleural effusion to 1 for calcification and cavity; specificity varied from 0.92 for opacity to 0.99 for fibrosis.

1.3.1 Inter-Radiologist Concordance

Inter-reader concordance is described in Table 2b. Concordance was highest on detection of abnormal X-rays (inter-reader agreement 85%, Cohen's Kappa 0.6, Fleiss' kappa 0.56).

1.3.2 Algorithm Accuracy Versus the Majority Opinion of 3 Radiologists

Figure 2:
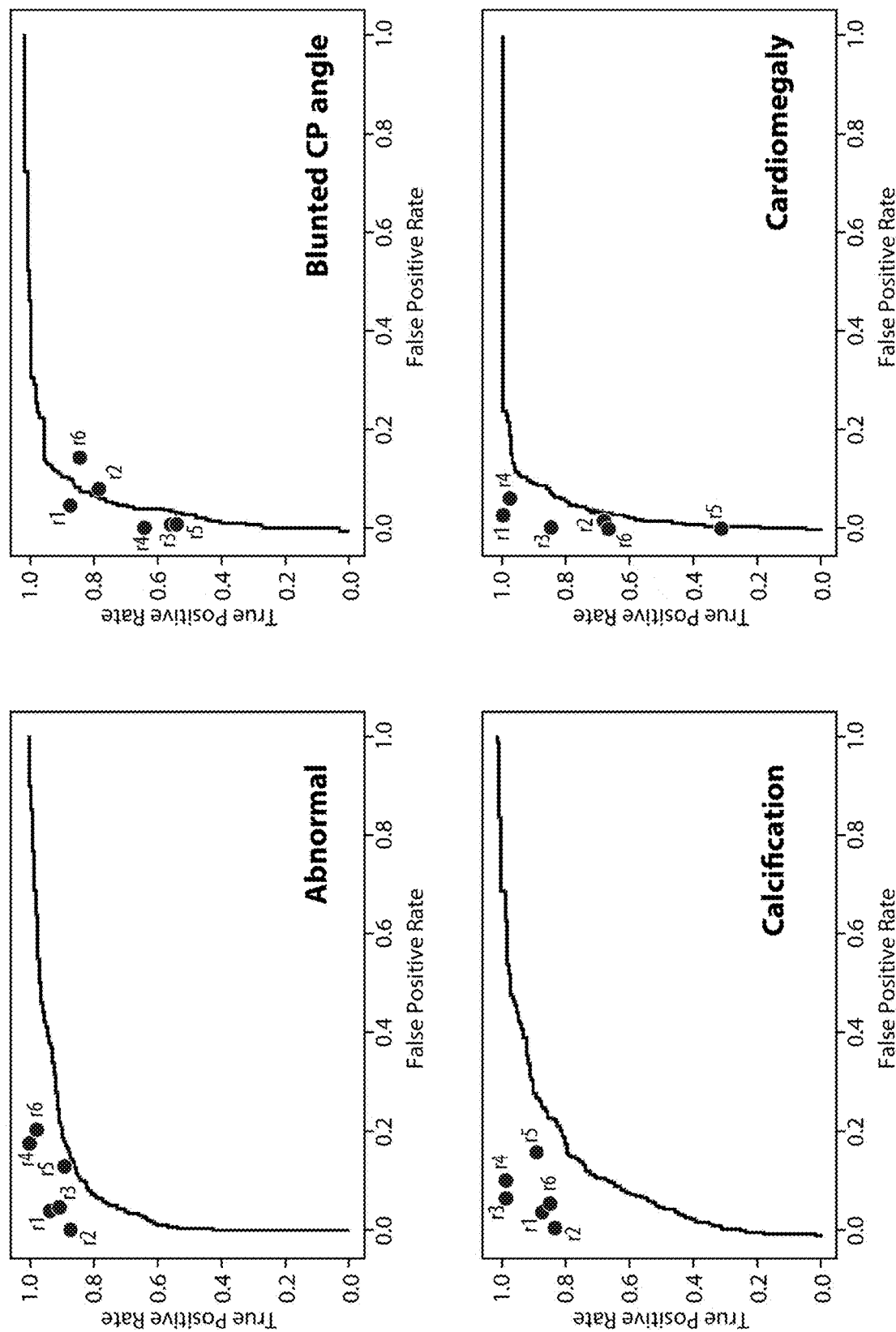
FIG. 2 AUC curves for all abnormalities versus a 3-radiologist majority, with reader performance marked.
Figure 2:
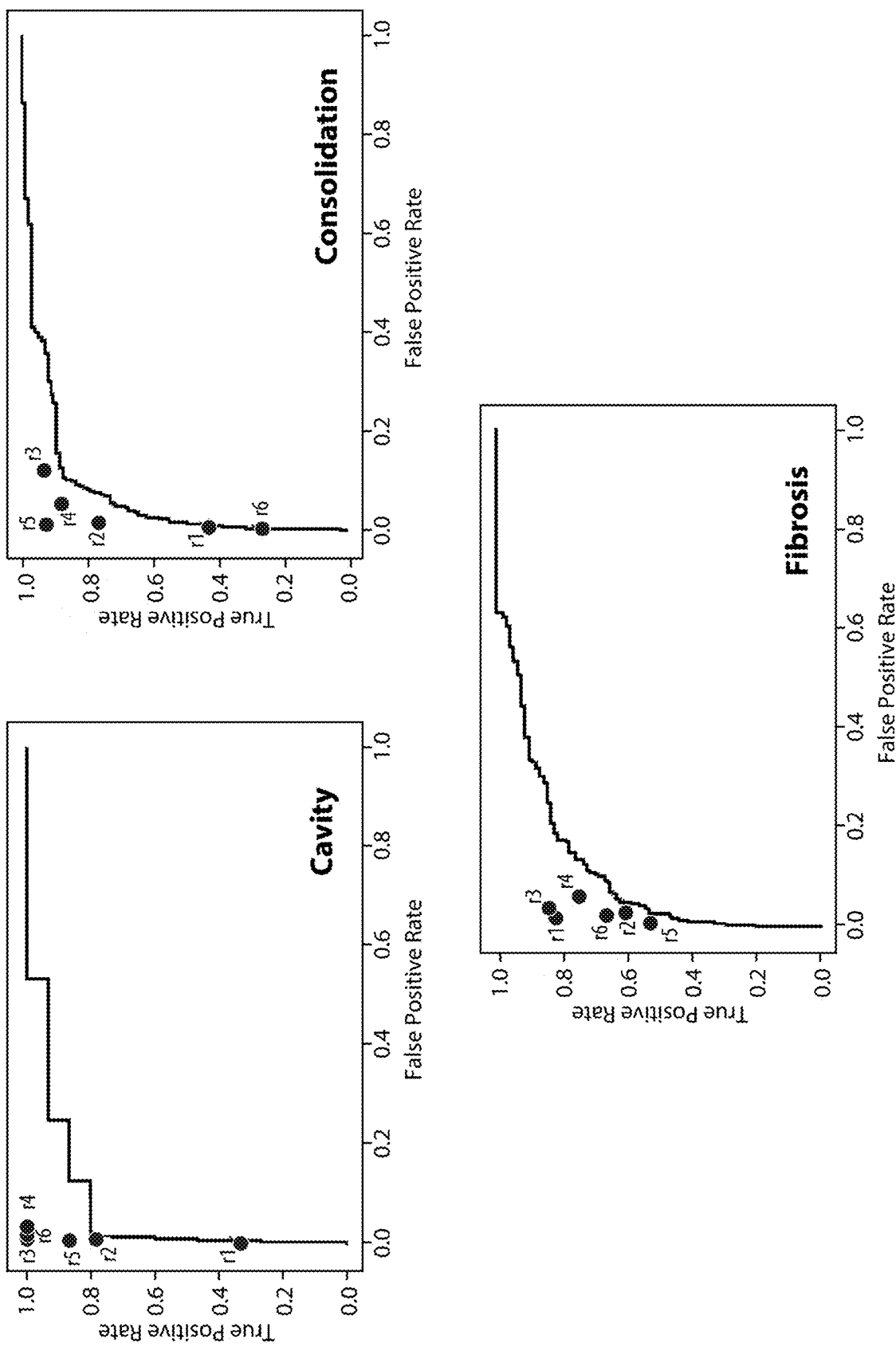
Figure 2:
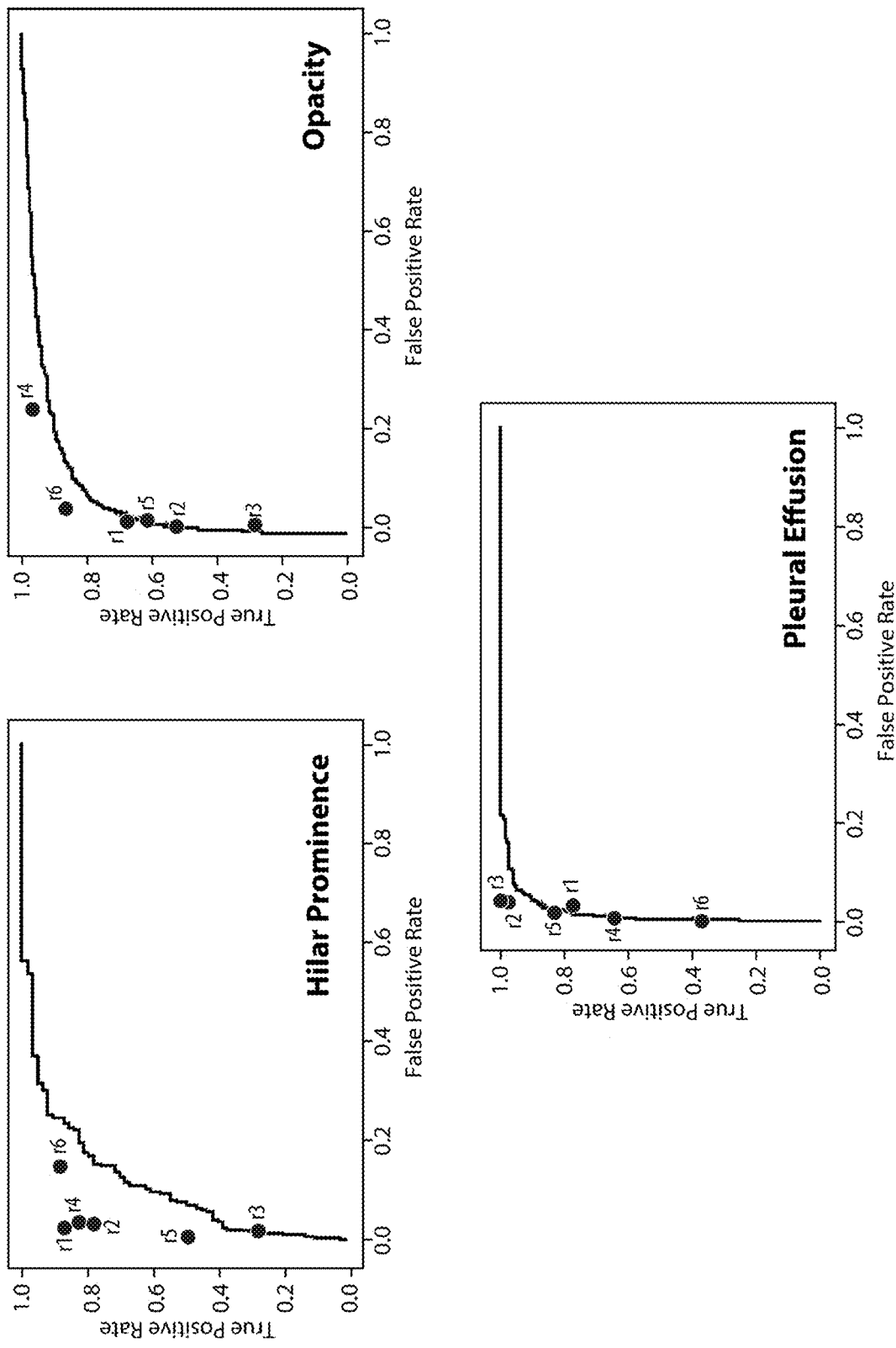

The deep learning system accuracy at identifying each of the 12 abnormalities is listed in Table 4. FIG. 2 shows AUC curves for each abnormality, plotted on the entire dataset (n=2000) versus the majority opinion of 3 radiologists (2 radiologists re-reading retrospectively, plus the original radiology report), drawn randomly out of a pool of 6 radiologists. Individual radiologist sensitivity and specificity for the 6 radiologists is marked on each plot. In most cases, individual radiologist sensitivity and specificity was slightly above the AUC curves, with exceptions for pleural effusion, cardiomegaly and opacity and where algorithm performance was equal to the performance of some individuals (or radiologist sensitivity and specificity).

TABLE 4

Performance of the algorithms

| Finding | AUC (95% CI) | High sensitivity operating point | | High specificity operating point | |
|---|---|---|---|---|---|
| | | Sensitivity | Specificity | Sensitivity | Specificity |
| Normal (No Abnormality Detected) | 0.9278 (0.9162-0.9394) | 0.9100 | 0.7519 | 0.8192 | 0.9086 |
| Blunted CP angle | 0.9434 (0.9179-0.9690) | 0.9487 | 0.7692 | 0.8461 | 0.9100 |
| Calcification | 0.8812 (0.8550-0.9073) | 0.9069 | 0.6550 | 0.6511 | 0.8912 |
| Cardiomegaly | 0.9670 (0.9484-0.9856) | 0.9717 | 0.8636 | 0.8474 | 0.9284 |
| Cavity | 0.9351 (0.8511-1.0000) | 0.9375 | 0.7528 | 0.8125 | 0.9850 |
| Consolidation | 0.9276 (0.8929-0.9623) | 0.9238 | 0.6970 | 0.8285 | 0.9112 |
| Fibrosis | 0.8851 (0.8436-0.9266) | 0.9000 | 0.6641 | 0.7454 | 0.8669 |
| Hilar Enlargement | 0.8908 (0.8379-0.9437) | 0.9218 | 0.7509 | 0.6718 | 0.8907 |
| Opacity | 0.9296 (0.9124-0.9468) | 0.9191 | 0.6991 | 0.8179 | 0.9097 |
| Pleural Effusion | 0.9841 (0.9703-0.9979) | 0.9810 | 0.8355 | 0.8797 | 0.9660 |

Another dataset (Qure90k) is randomly sampled across 4 centers in India that did not contribute to the original training dataset. The Standard of Reference (Ground Truth) for this dataset is established using Natural Language Processing (NLP) on original radiologist reports. The deep learning system accuracy at identifying each of the 12 abnormalities is listed in Table 5.

TABLE 5

Performance of the algorithms on Qure90K dataset.

| Finding | AUC (95% CI) | High sensitivity operating point | | High specificity operating point | |
|---|---|---|---|---|---|
| | | Sensitivity | Specificity | Sensitivity | Specificity |
| Normal (No Abnormality Detected) | 0.8436 (0.8314-0.8558) | 0.9000 | 0.6419 | 0.6918 | 0.9000 |
| Blunted CP angle | 0.9141 (0.9060-0.9223) | 0.9000 | 0.7406 | 0.7885 | 0.9000 |
| Calcification | 0.8622 (0.8360-0.8883) | 0.9000 | 0.6246 | 0.6736 | 0.8815 |
| Cardiomegaly | 0.9369 (0.9312-0.9426) | 0.9000 | 0.8450 | 0.8439 | 0.9000 |
| Cavity | 0.9356 (0.9104-0.9608) | 0.9000 | 0.8268 | 0.8636 | 0.9000 |
| Consolidation | 0.9180 (0.9092-0.9267) | 0.9000 | 0.8101 | 0.7873 | 0.9000 |
| Fibrosis | 0.8916 (0.8783-0.9049) | 0.9000 | 0.6512 | 0.7302 | 0.9000 |
| Hilar Enlargement | 0.8501 (0.8379-0.9437) | 0.9000 | 0.5597 | 0.6022 | 0.9000 |
| Opacity | 0.8948 (0.8898-0.8998) | 0.9000 | 0.7321 | 0.7800 | 0.9000 |
| Pleural Effusion | 0.9076 (0.9009-0.9144) | 0.9000 | 0.7433 | 0.7914 | 0.9000 |

1.4 Conclusion

The deep learning system demonstrated an AUC of 0.93 (CI 0.92-0.94) for detection of abnormal scans, and AUC (CI) of 0.94 (0.92-0.97), 0.88 (0.85-0.91), 0.97 (0.95-0.99), 0.93 (0.85-1), 0.93 (0.89-0.96), 0.88 (0.84-0.93), 0.89 (0.84-0.94), 0.93 (0.91-0.95), 0.98 (0.97-1) for the detection of blunted costophrenic angle, calcification, cardiomegaly, cavity, consolidation, fibrosis, hilar enlargement, opacity and pleural effusion respectively.

This example shows that a deep learning algorithm trained with large amounts of well-labeled data can accurately detect abnormalities on chest X-rays. As these systems get more accurate, the feasibility of using them to extend the reach of chest X-ray interpretation and improve its efficiency increases.

Example 2. Deep Learning Solution qXR for Tuberculosis Detection

Qure.ai's qXR is designed to screen and prioritize abnormal chest X-rays. The algorithm automatically identifies 15 most common chest X-ray abnormalities. A subset of these abnormalities that suggest typical or atypical pulmonary Tuberculosis are combined to generate a 'Tuberculosis screening' algorithm within the product. The tuberculosis screening algorithm is intended to replicate a radiologist or physician's screen of chest X-rays for abnormalities suggestive of Tuberculosis, before microbiological confirmation. qXR is the first AI based Chest X-ray interpretation software to be CE certified. qXR integrates with Vendor Neutral Integration Process and works with X-rays generated from any X-ray system (CR or DR). qXR screens for Tuberculosis and also identifies 15 other abnormalities, so that patients can be informed about non-TB conditions they might be suffering from.

qXR seamlessly integrates with Vendor Neutral Archives (VNA) and PACS without interfering with the existing Radiology workflow. It is deployed in HIPAA compliant cloud servers to deliver a table of results containing:
  a. 'Normal' or 'abnormal' for each chest X-ray
  b. List of all abnormalities detected by the algorithm with its corresponding probability scores.
  c. 'Tuberculosis screen advised' or 'tuberculosis screen negative' for each X-ray, with probability scores.

Figure 3:
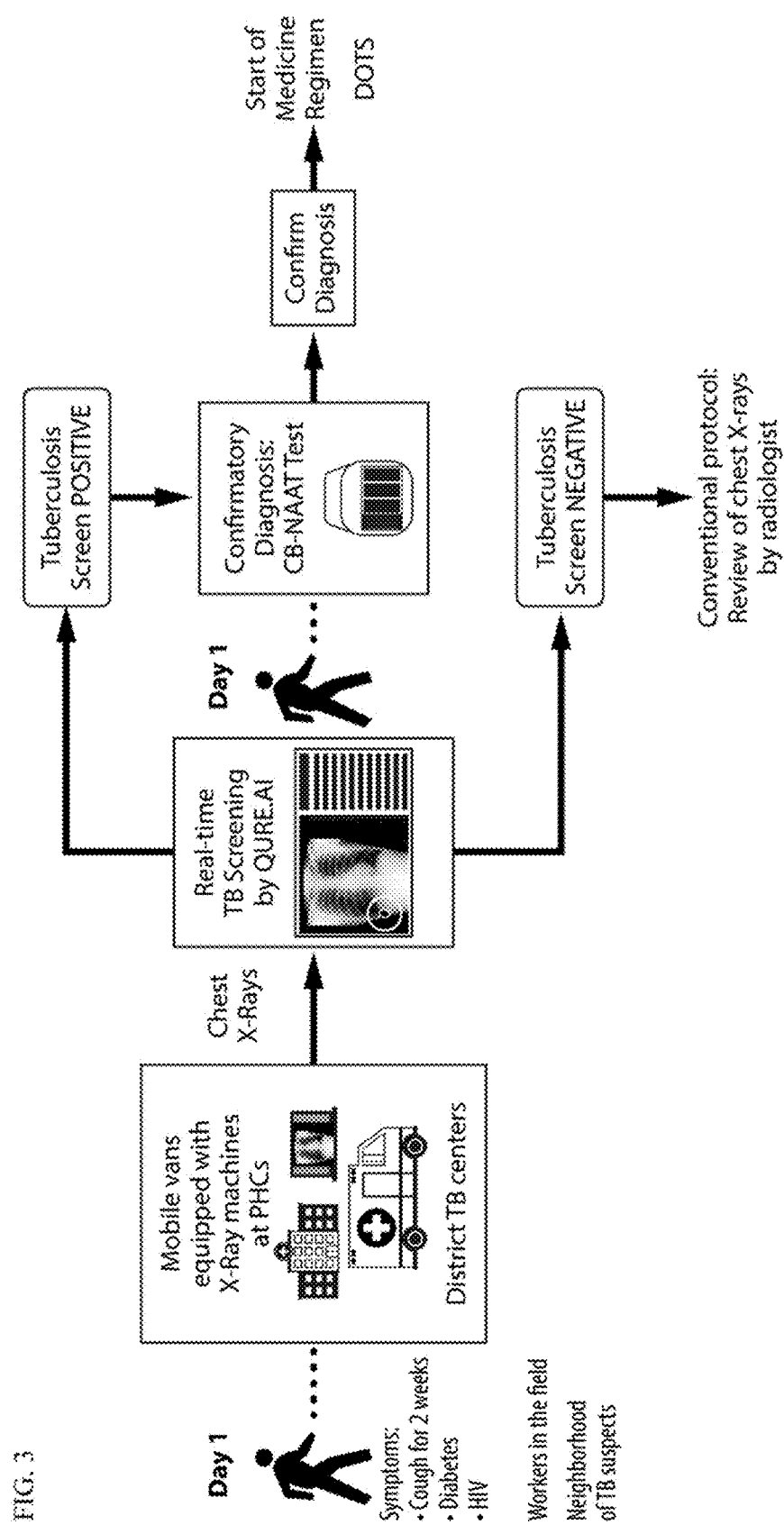
FIG. 3 Proposed workflow for TB detection using qXR for pilot at district TB centers.

Using standard imaging protocols, qXR automatically uploads the X-rays of interest (anonymized) from the client PACS/VNA and responds back with the results overlay and corresponding reports using HL7 formats, allowing the user to have access to analysis prior to review of original X-rays. This standard process, ensures that individuals with symptoms like cough over two weeks, diabetes and other immunocompromised patients get their screening for Tuberculosis done within seconds, referred for microbiological confirmation (NAAT) and if found positive, the treatment can start the same day. FIG. 3 shows the proposed workflow for TB detection using qXR for pilot at district TB centers.

The deployment efforts will involve integrating with current X-ray system through an API. The results are compatible with any radiology viewer or can be hosted on a web-based Qure viewer. The automated report is created with scores that correspond to a level of recognition of the characteristics of the particular medical condition in the image data. Table 6 is an example of the automated report.

TABLE 6

An example of the automated report.
Chest X-Ray abnormality detection and scoring

| X-Ray Findings | Probability | Remark |
|---|---|---|
| Abnormal | 0.94 | YES |
| Blunted Costophrenic angle | 0.24 | NO |
| Calcification | 0.78 | YES |
| Cardiomegaly | 0.11 | NO |
| Cavity | 0.85 | YES |
| Cervical Rib | 0.42 | NO |

TABLE 6-continued

An example of the automated report.
Chest X-Ray abnormality detection and scoring

| X-Ray Findings | Probability | Remark |
| --- | --- | --- |
| Consolidation | 0.92 | YES |
| Hyper Inflation | 0.44 | NO |
| Fibrosis | 0.8 | YES |
| Prominence in Hilar region | 0.91 | YES |
| Opacity | 0.95 | YES |
| Pleural Effusion | 0.08 | NO |
| Scoliosis | 0.1 | NO |
| Tuberculosis screen | 0.96 | ADVISED |

We claim:

1. A method for streamlining tuberculosis detection by automating an X-ray screening and prioritizing process, comprising:
receiving and processing images from chest X-ray scan imaging procedure data;
detecting and localizing medical abnormalities of the images using a deep learning system, wherein the deep learning system carried out by a computer is developed by the steps of:
selecting medical imaging scans and extracting the medical abnormalities using natural language processing (NLP) algorithms, wherein the medical abnormalities comprise blunted costophrenic angle, calcification, cardiomegaly, cavity, cervical rib, consolidation, hyper inflation, fibrosis, prominence in hilar region, opacity, pleural effusion, and scoliosis;
pre-processing the selected medical imaging scans by resizing and tag-specific data augmentations;
training a deep learning algorithm with the selected medical imaging scans;
predicting the presence or absence of a particular type of medical abnormalities by combining the predictions of multiple classification models using different initial conditions, architectures and sampling via a majority ensembling scheme, wherein the multiple classification models are pre-trained on a task of separating chest X-rays from X-rays of other body parts; and
generating a score that corresponds to a level of recognition of each of the medical abnormalities and outputting a bounding box representing the precise location and extent of the medical abnormalities; and
generating another score and advice that corresponds to a level of recognition of tuberculosis based on the scores of the medical abnormalities that suggest typical or atypical tuberculosis.

2. The method of claim 1, wherein the deep learning algorithm comprises a convolutional neural network architecture.

3. The method of claim 2, wherein the architecture is modified by pre-training on the task of separating chest X-rays from X-rays of other body parts.

4. The method of claim 1, wherein the models are selected using various heuristics.

5. The method of claim 1, wherein the accuracy of the deep learning algorithm for detecting the medical abnormalities is validated by comparing with radiologist reports.

6. A system for streamlining tuberculosis detection by automating an X-ray screening and prioritizing process, comprising:
a computing device configured to receive and process images from chest X-ray scan imaging procedure data;
the computing device configured to detect and localize medical abnormalities of the images using a deep learning system, wherein the deep learning system is developed by the steps of:
selecting medical imaging scans and extracting the medical abnormalities using natural language processing (NLP) algorithms, wherein the medical abnormalities comprise blunted costophrenic angle, calcification, cardiomegaly, cavity, cervical rib, consolidation, hyper inflation, fibrosis, prominence in hilar region, opacity, pleural effusion, and scoliosis;
pre-processing the selected medical imaging scans by resizing and tag-specific data augmentations;
training a deep learning algorithm with the selected medical imaging scans;
predicting the presence or absence of a particular type of medical abnormalities by combining the predictions of multiple classification models using different initial conditions, architectures and sampling via a majority ensembling scheme, wherein the multiple classification models are pre-trained on a task of separating chest X-rays from X-rays of other body parts; and
generating a score that corresponds to a level of recognition of each of the medical abnormalities and outputting a bounding box representing the precise location and extent of the medical abnormalities; and
the computing device configured to generate another score and advice that corresponds to a level of recognition of tuberculosis based on the scores of the medical abnormalities that suggest typical or atypical tuberculosis.

7. The system of claim 6, wherein the deep learning algorithm comprises a convolutional neural network architecture.

8. The system of claim 7, wherein the architecture is modified by pre-training on the task of separating chest X-rays from X-rays of other body parts.

9. The system of claim 6, wherein the models are selected using various heuristics.

10. The system of claim 6, wherein the accuracy of the deep learning algorithm for detecting the medical abnormalities is validated by comparing with radiologist reports.

11. The system of claim 6, wherein the algorithms achieve Area under the Receiver Operating Characteristic curve (AUC) of $0.93\pm0.01$ for detection of abnormal scans, and AUCs of $0.94\pm0.02$, $0.88\pm0.03$, $0.97\pm0.02$, $0.93\pm0.07$, $0.93\pm0.04$, $0.88\pm0.05$, $0.89\pm0.05$, $0.93\pm0.02$, $0.98\pm0.02$ for the detection of blunted costophrenic angle, calcification, cardiomegaly, cavity, consolidation, fibrosis, hilar enlargement, opacity and pleural effusion, respectively.

* * * * *